US 7,022,065 B2

United States Patent
Leiner et al.

(10) Patent No.: US 7,022,065 B2
(45) Date of Patent: Apr. 4, 2006

(54) ENDOSCOPE TEST DEVICE

(75) Inventors: Dennis C. Leiner, Cape Elizabeth, ME (US); Michael Bush, South Portland, ME (US)

(73) Assignee: Lighthouse Imaging Corporation, Portland, ME (US)

( * ) Notice: Subject to any disclaimer, the term of this patent is extended or adjusted under 35 U.S.C. 154(b) by 59 days.

(21) Appl. No.: 10/910,074

(22) Filed: Aug. 3, 2004

(65) Prior Publication Data
US 2005/0049457 A1 Mar. 3, 2005

Related U.S. Application Data

(60) Provisional application No. 60/498,201, filed on Aug. 27, 2003.

(51) Int. Cl.
*A61B 1/00* (2006.01)
(52) U.S. Cl. .................. 600/101; 600/117; 600/127; 356/73.1; 356/124
(58) Field of Classification Search ............. 600/101, 600/117, 127; 356/73.1
See application file for complete search history.

(56) References Cited

U.S. PATENT DOCUMENTS

| | | | | |
|---|---|---|---|---|
| 4,607,923 | A | | 8/1986 | Task et al. ............ 351/239 |
| 5,820,547 | A | * | 10/1998 | Strobl et al. ............ 600/127 |
| 6,069,691 | A | * | 5/2000 | Rosow et al. ............ 356/124.5 |
| 6,203,492 | B1 | * | 3/2001 | Davis ............ 600/101 |
| 6,498,642 | B1 | * | 12/2002 | Duckett ............ 356/244 |
| 6,673,011 | B1 | * | 1/2004 | Hilger ............ 600/117 |
| 6,833,912 | B1 | * | 12/2004 | Lei et al. ............ 356/124 |

OTHER PUBLICATIONS

Pinkus, Alan, et al., Measuring Observers' Visual Acuity Through Night Vision Goggles, Air Force Research Laboratory, Wright-Patterson AFB, OH, Aug. 25, 1988.
Endoscopy System Testing Kit, BC Group International (www.bcgroupintl.com), St. Louis, MO.
EndoBench, Lighthouse Imaging Corporation (www.lighthouseoptics.com), Portland, ME.
The EndoTester, National Instruments (www.ni.com), Austin, TX.
EQ-Test, Sri Comm Instruments (www.sci.com.my), Kuala Lumpur, Malaysia.
Dale 301, BC Group International (www.bcgroup.com), St. Louis, MO.

* cited by examiner

*Primary Examiner*—Beverly M. Flanagan
*Assistant Examiner*—Matthew J. Kasztejna
(74) *Attorney, Agent, or Firm*—Francis J. Caufield (57) ABSTRACT

The invention uses optics and precision mechanisms to quantitatively assess the performance of medical endoscopes. By viewing standardized optical targets under well-controlled conditions, the optical quality of endoscopes can be easily determined in much the same fashion as getting one's eyes tested at the optometrist. The actual design, however, is much more complicated than your optometrist's eye chart and different types of endoscopes from different manufacturers require customization of the target geometry, the viewing distance, and the viewing angle. Also, there are several optical characteristics beyond image sharpness that need to be assessed, requiring other unique test geometries, including contrast, distortion, and vignetting. Clinically significant measurements are performed with simplicity and cost-effectiveness through the use of relatively inexpensive optical components and an embedded processor and graphical display system.

21 Claims, 10 Drawing Sheets

SECTION A-A

ENDOSCOPE TEST DEVICE

CROSS-REFERENCE TO RELATED APPLICATION

This application claims the benefit of priority from U.S. Provisional Patent Application No. 60/498,201 filed on Aug. 27, 2003 in the name of Dennis C. Leiner, et al. with the title ENDOSCOPE TEST DEVICE, the entire contents of which are incorporated herein by reference.

FIELD OF THE INVENTION

This invention generally relates to apparatus and methodology for testing certain optical characteristics of medical endoscopes and borescopes and, more particularly, to apparatus and methodology for quantifying the quality of imaging through endoscopes and borescopes by providing tests for, including but not limited to, contrast, distortion, transmission, uniformity, and vignetting. The invention employs a CPU with a display device to generate specially formatted target images to an observer who then executes various scripted testing procedures that ultimately lead to a figure of merit for performance.

BACKGROUND OF THE INVENTION

The United States endoscopy market size in 1999 was $3.6 Billion. Visualization products, which include rigid endoscopes, light sources and video accessories, represent a 17%, or more, segment of this market valued at more than $600 Million. According to Stryker Corporation's 1999 Fact Book, the world endoscopy market approaches $6 Billion, and the market for visualization products continues to grow at 8–10% per year.

Of the 5,000 hospitals in the U.S., some 4,200 have 4 to 6 operating rooms. The remaining 800 hospitals have between 6 and 70 operating rooms. It is reasonable to assume that at least half of the estimated 30,000 operating rooms in the U.S. are equipped to perform endoscopic surgery. In addition to hospital ORs, there exist more than 14,000 medical offices with surgery suites. Again, it is reasonable to assume that half of these office-based surgery facilities perform endoscopic procedures. Collectively, these hospitals and surgery centers, with more than 20,000 endoscopic operating rooms, form the 12,000 unit principal market for the invention.

A secondary market involves third-party endoscope repair organizations. Often these repair companies enter into contracts with hospitals and surgical centers to capitate repair expenses for endoscopes. Typically, such contracts guarantee that all the endoscopes in a facility are kept in working order. The installation of an endoscope tester at these contract facilities enables both the hospital and the repair company to quantitatively assess the endoscopes before and after repair, reducing unneeded repair costs.

Endoscopes are complex optical instruments, often containing more than 30 tiny lens components. By their very nature, these devices are prone to failure from:

Overstressing during surgery (particularly orthopedic)
Carelessness during sterilization reprocessing
Poor manufacturing design or workmanship
Wear-and-tear after many sterilization cycles.
Improper repair, especially by unauthorized repair facilities With costs ranging from $2,000 to more than $20,000, it is important to efficiently repair and keep endoscopes in use as long as possible. Unfortunately, there are currently no instruments available that provide hospitals with the clinically important and 0quantitative measurements to help determine whether an endoscope is fit for surgery.

There are three products that seek to address the need for quantitative endoscope measurements. None, however, meet the market's need for a cost-effective device that can be used in a clinical environment.

One instrument is the Lighthouse Imaging Corporation EndoBench™ tester. The advantage of the EndoBench™ tester is that it provides all of the clinically significant data to determine if an endoscope is suitable for surgery. Its cost and complexity, however, make it most suitable to a manufacturing environment.

Premise Development Corporation advertises a device called the Endotester. Like the EndoBench™ tester, this instrument performs most of the important optical measurements. Unfortunately, the Endotester requires a custom computer system and appears to be complicated to use. In addition, the Endotester is still in breadboard form and does not perform calibrated measurements, making the device of limited value in comparing test endoscopes to reference endoscopes.

DNI Nevada, Inc. manufactures the EQ-Test Endoscopy Test System. This system addresses the same market as the invention and is simple to operate. The EQ-Test does not, however, provide the needed measurements for the assessment of image quality; it only assesses the photometric characteristics of endoscopes. And, while interesting to the engineer and scientist, photometric characteristics of an endoscope are not particularly important clinically. In addition, photometry is rarely, if ever, a failure mode in endoscope usage.

The limitation of performing endoscope quality tests without a computer frame-grab system is that when viewing an endoscope image with the eye, the limiting resolution of the endoscope is fairly well matched to the limiting resolution of the eye itself. This is appropriate from an optical design point of view. It is difficult, however, from a measurement standpoint. For example, the eye at the end of a long day becomes tired and may not perform as well as in the morning. Therefore, an endoscope measurement at the end of the day may appear worse than at the beginning since it was the eye that became defective and not the endoscope.

Consequently, there is a need for a low-cost solution for testing. endoscopes and borescopes that provides the benefits of a frame-grab system and, conducts clinically significant tests beyond measurements of photometric properties, and it is a primary object to the invention to satisfy this need.

It is another object of the invention to provide apparatus and methodology for testing an endoscope or borescope by assessing the visual acuity of an observer viewing test targets through the endoscope while minimizing the impact of the, observers visual system on the results of the test.

Other objects of the invention will, in part, be obvious and others will, in part, appear hereinafter when the following detailed description is read in connection with the drawings.

SUMMARY OF THE INVENTION

The invention provides an apparatus and methodology for quantitatively measuring the fitness of an endoscope for use in surgical procedures. The invention comprises a compact embedded processor which generates test patterns to a compact graphical display device, that are observed through an optical system that magnifies the image between the endoscope and the eye. The magnified images ease the burden on an operator's eye so that the measurements performed assess only the endoscope, not the combination of endoscope and eye. Specifically, the eye has a resolution of approximately 1 minute of arc. This is also approximately the resolution of the best quality endoscopes. The optical system magnifies the angular size of the image exiting the endoscope preferably by between 1.5–3×. Therefore, since the eye retains its 1 minute resolution, it needs to resolve only 1.5–3 minutes of arc at the least to assure that the endoscope, and not the observer, is measured.

The images are linked to software instructions provided to the observer to guide the observer through a series of sequential steps by which the observer grades his visual response to the targets. The statistics of the observer's responses and corresponding visual targets are processed to calculate a figure of merit for the fitness of the endoscope compared with specifications or baseline measurements. In calculating the figure of merit, different test outcomes are weighted differently depending on their assigned importance in clinical settings.

BRIEF DESCRIPTION OF THE DRAWINGS

The structure, operation, and methodology of the invention, together with other objects and advantages thereof, may best be understood by reading the detailed description in conjunction with the drawings in which each part has an assigned numeral or label that identifies it wherever it appears in the various drawings and wherein:

FIG. 3b is an elevational view of the apparatus shown in FIG. 3a;

FIG. 3d is an end view of the apparatus of FIG. 3a;

DETAILED DESCRIPTION

Figure 1A:
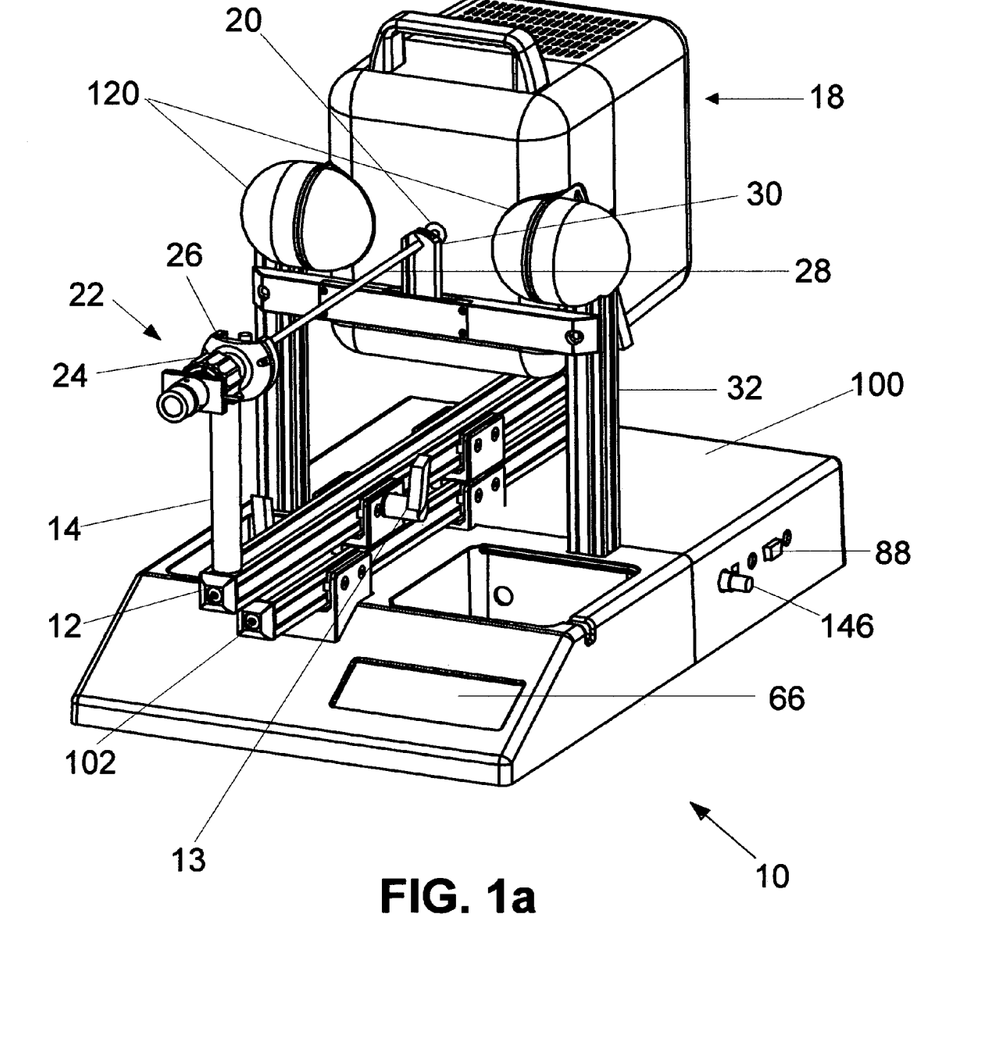
FIG. 1a is a diagrammatic perspective view illustrating the major components of the endoscope tester of the invention.
Figure 1B:
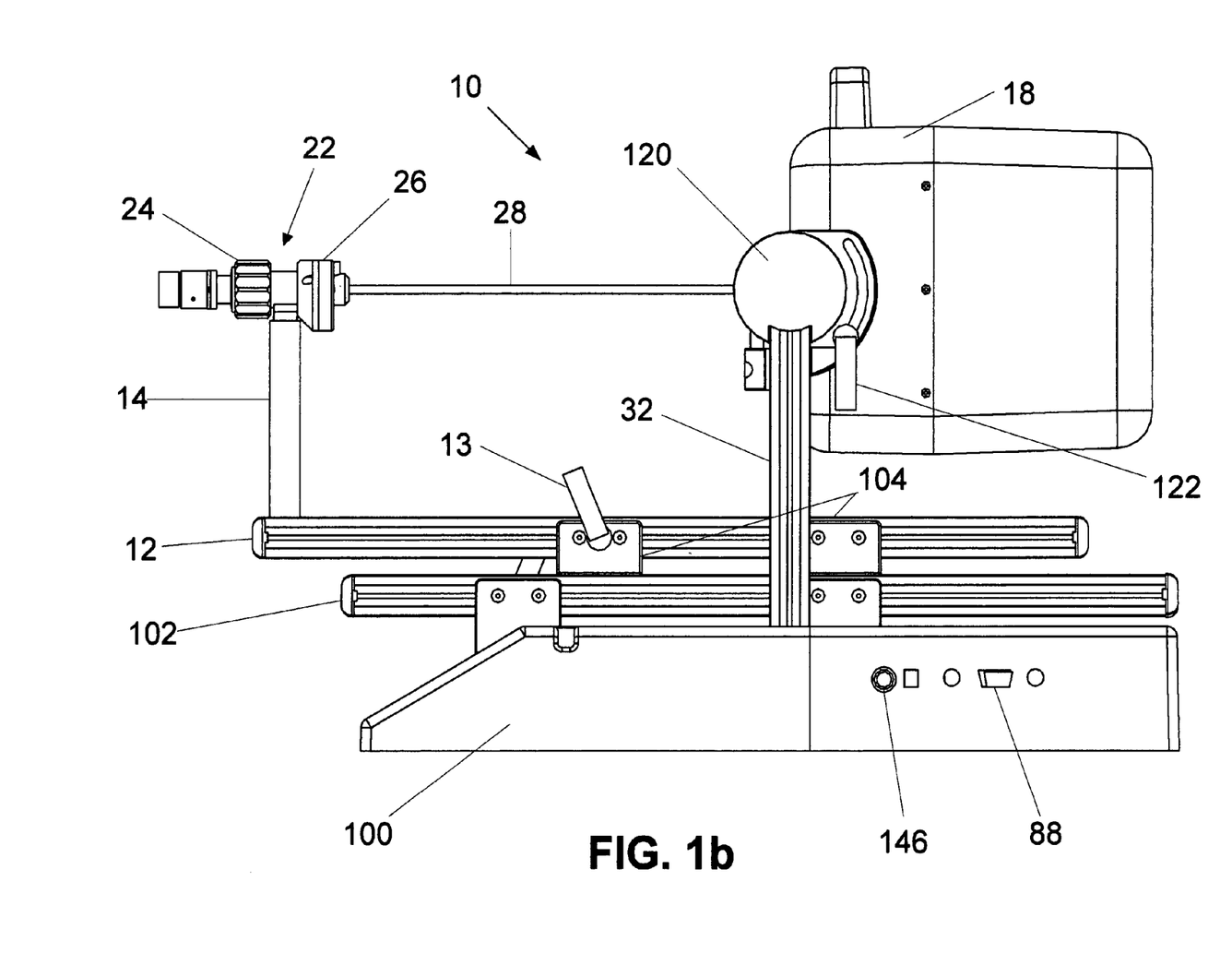
FIG. 1b is a diagrammatic side elevational view of the endoscope tester of FIG. 1a showing its major components in profile.
Figure 1C:
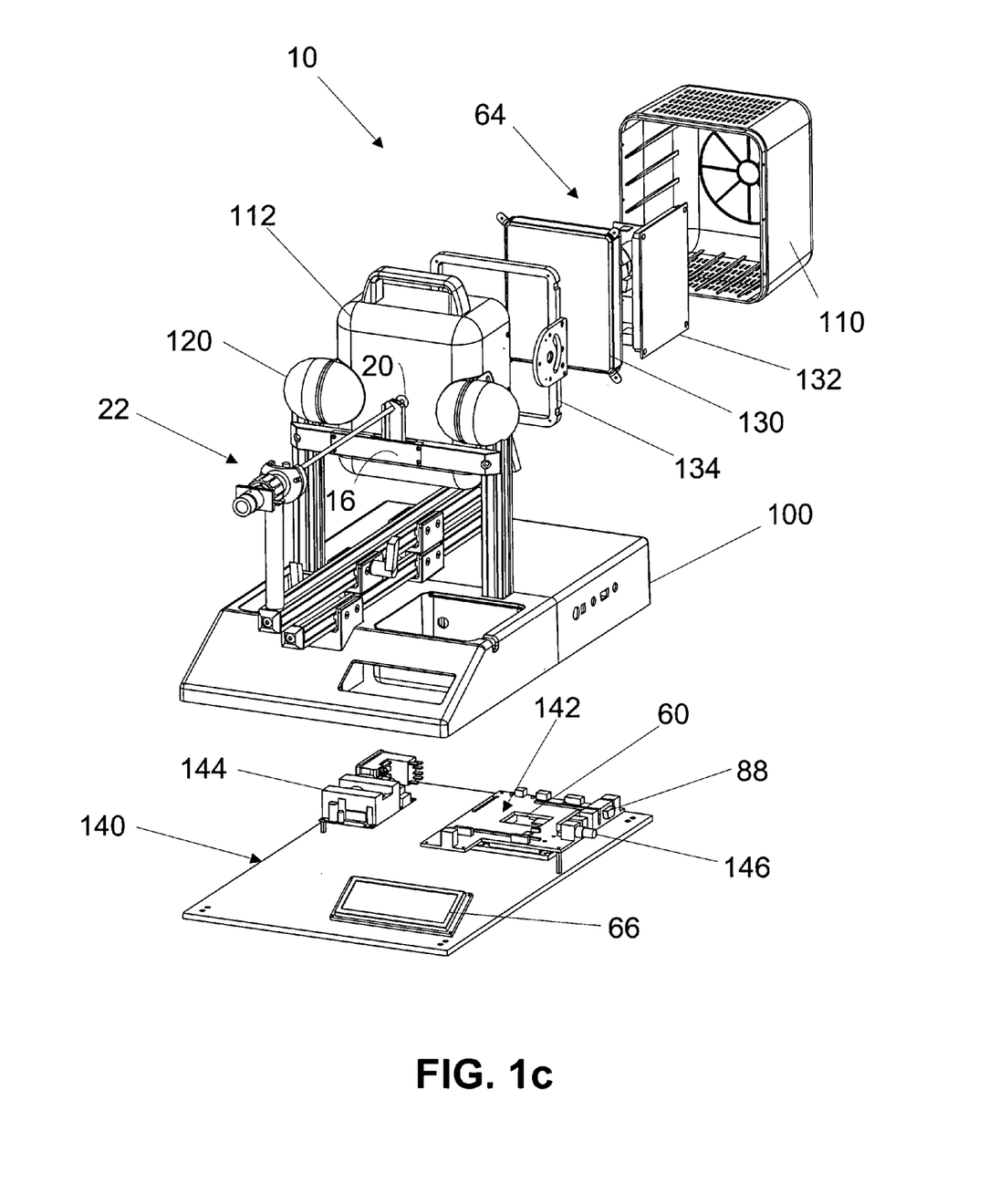
FIG. 1c is a diagrammatic exploded perspective view of the endoscope tester of FIGS. 1a and 1b.

Reference is now made to FIGS. 1a–1c which show the inventive endoscope test system generally at 10. In a manner to be described, system 10 quantitatively measures the fitness of an endoscope for use in surgical procedures by generating user selectable predetermined test specific patterns on a compact graphical display device. The test patterns are observed through an optical system that magnifies the image between the endoscope and the eye, and the quality of the observed test patterns are scored by the observer and processed by system 10 that calculates a performance figure of merit indicating the endoscope's fitness for clinical use.

The major components of system 10 comprise a longitudinally extending rail 12 on which is mounted a slideable, vertically extending support 14. Above longitudinally extending rail 12 is a fixedly positioned cross frame member 16. Pivotally attached to cross frame member frame 16 is a housing 18 containing various electronics. Referring now to FIG. 1c, which is an exploded view of system 10 generally, there can be seen a support frame 134 that carries the various electronics including a display 130, preferably a high resolution CRT, and display electronics 132. Referring now to FIG. 1b, which is a side elevational view of system 10 generally, it can be seen that housing 18 comprises front 112 and rear 110 cases, respectively, which are detachable for accessing enclosed electronics. Front case 112 is also provided with an aperture stop 20.

Referring to FIGS. 1a and 1b, it can be seen that atop support 14 is mounted an ocular and nest assembly 22 which contains a 1.5–3× eyepiece or ocular 24 and nest 26 for slideably receiving the proximal end of an endoscope to be tested, which is generally designed at 28. Nest 26 is configured to receive a variety of different endoscopes as needed. The distal end of endoscope 28 is supported with a mechanical clamping arrangement 30 that is slideably mounted on cross frame member 16. Clamping arrangement 30 automatically centers the mechanical axis of endoscope 28 with respect to the center of aperture stop 20 thus placing the nominal optical axis of endoscope 28 on the center of the aperture stop 20, as well. Ocular and nest assembly 22 may be moved in concert with post 14 and extending rail 12 to longitudinally position the distal end of the endoscope with respect to aperture stop 20 to adjust the viewable field of the endoscope. Referring to FIG. 1b, it can be seen that extending rail 12 is slideable along supports 104, and can be locked and released via lever 13.

The angle of housing 18 along with attached aperture stop 20 is adjusted via torsion spring assemblies 120 to align the CRT display 130 so that it is always nominally perpendicular to the field of view of endoscope 28. This feature is especially useful when measuring side looking endoscopes that are typically provided with side viewing angles that may be up to 90 degrees off the mechanical axis. Shown in FIG. 1b, alignment lock 122 is used to lock and release the alignment mechanism.

Now referring to FIG. 1c, it can be seen that a base enclosure 100 contains and protects various electronic components, including a base electronics board 140, to which are attached a power supply and regulator 144, an electronics board 142, and an LCD display 66. A CPU 60 drives control of test processes and data, including display output, external inputs and data outputs. External connectors 88 are used to interface with peripherals and for transmitting and receiving data, instructions, and/or software revisions. LCD 66 may be used to display data and the functional status of system 10.

Figure 2:
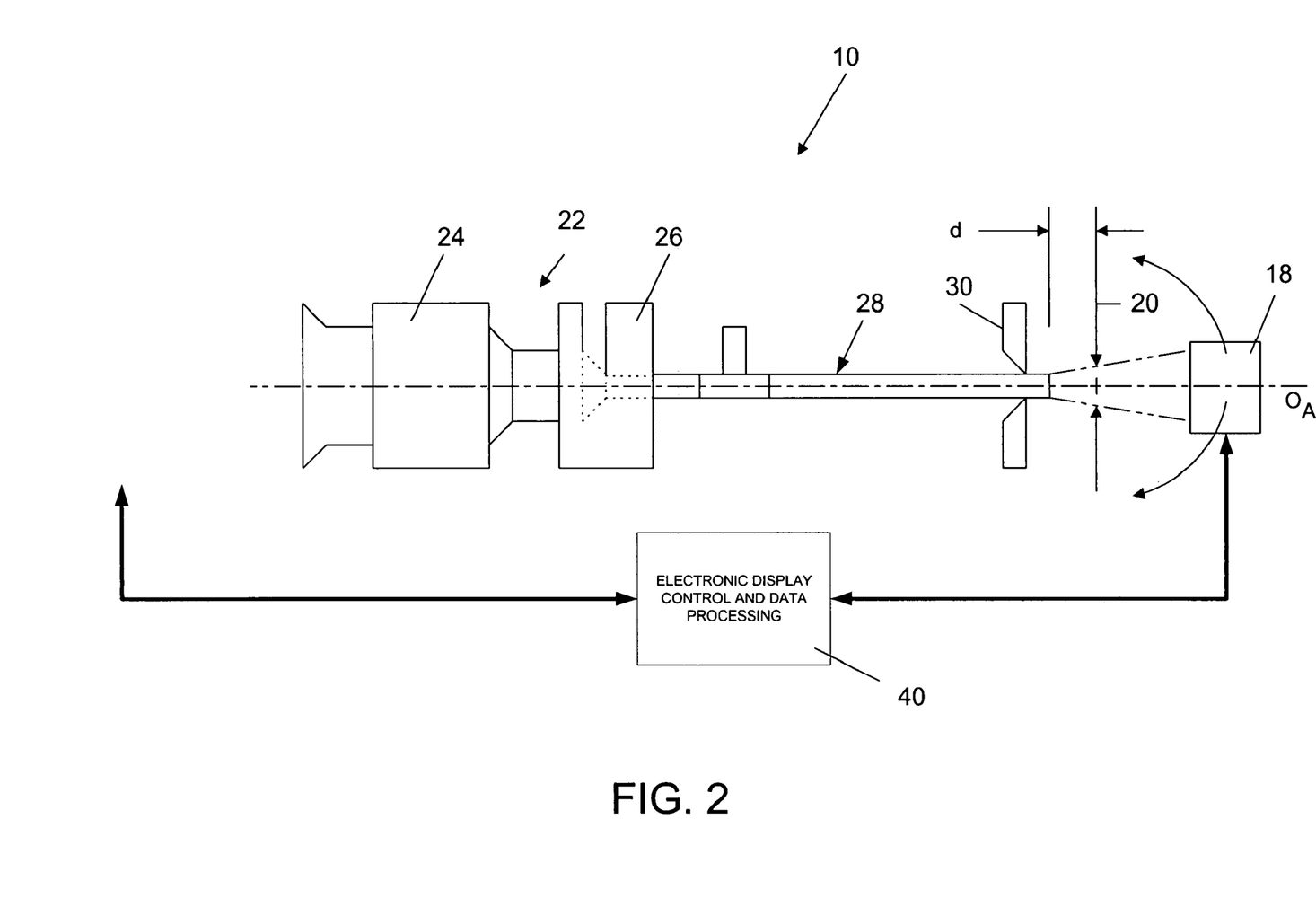
FIG. 2 is a simplified diagrammatic elevational view of the tester of FIGS. 1a–1c.

Reference is now made to FIG. 2, which additionally shows that the electronics board 142, LCD 66, and CPU 60 of system 10 comprise an electronic display control data processing subsystem 40 for generating images on the system display CRT 130 and exchanging control signals and data between the system's components. User inputs are preferably made via a keyboard or other equivalent interface, such as LCD screen 66.

Figure 3A:
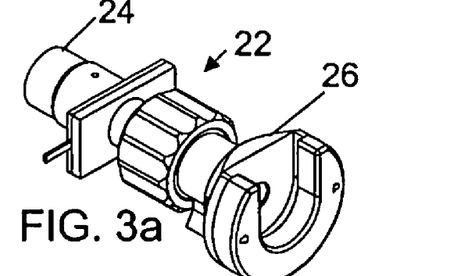
FIG. 3a is a diagrammatic perspective view of the mechanical design of the ocular and nest for supporting the proximal end of an endoscope with respect to the ocular.
Figure 3B:
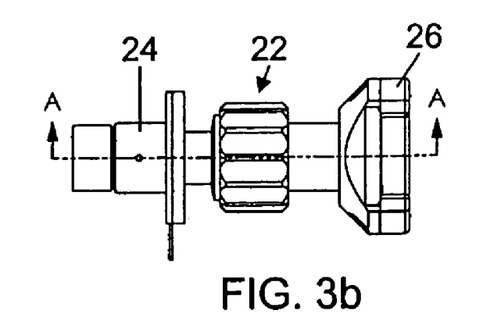
Figure 3C:
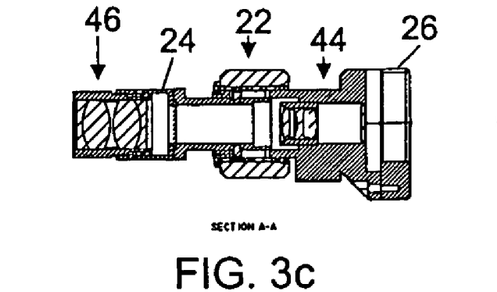
FIG. 3c is a diagrammatic sectional view of the apparatus of FIG. 3b taken along lines A—A therein.
Figure 3D:
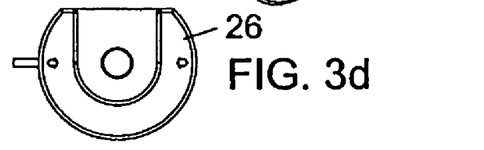

Reference is now made to FIGS. 3a through 3d, which show the mechanical and optical features of the ocular and nest assembly 22. As seen in those figures, the nest is configured and arranged to slideably receive the proximal end of endoscope 28 via a sideways entrance and removal action, thus providing a, simple means for receiving and positioning the distal end with respect to an ocular section or ocular 24. As shown in FIG. 3c, ocular 24 comprises a relay section 44 and an eyepiece 46.

Figure 3E:
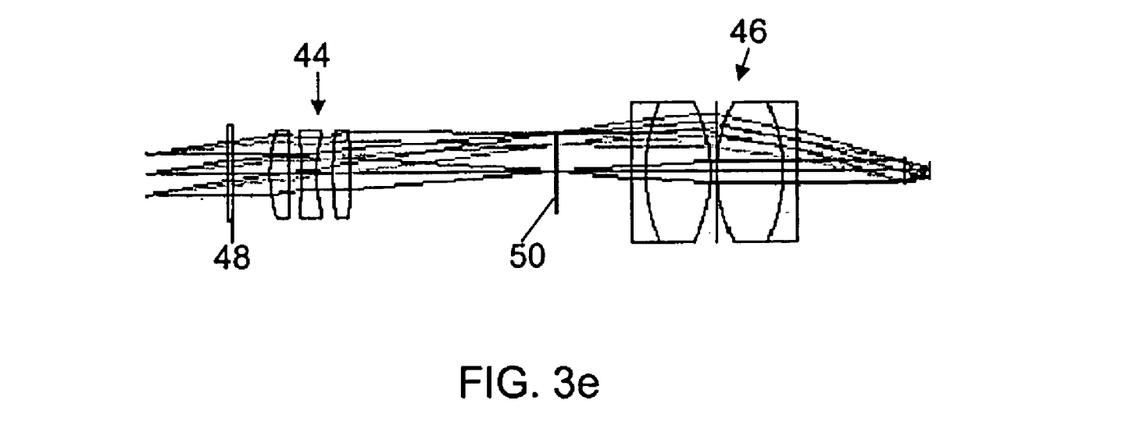
FIG. 3e is a diagrammatic elevational view of the optical elements of the magnifying ocular of the invention shown with ray tracings.

FIG. 3e shows one optical design for the ocular 24 of the invention. As seen in FIG. 3e, ocular 24 is a telescope comprising a three-element lens as relay section 44 and a two-element lens as eyepiece 46. The image presented to an endoscope under test is formed at the proximal end where it is designated in FIG. 3e as 48. Relay system 44 forms an intermediate image of image 48. The intermediate image is designated at 50 and is formed between relay section 44 and eyepiece 46. Eyepiece 46 forms, for example, a 2X magnified image of intermediate image 50 and presents it to the eye of an observer.

The optical design of the ocular 24 is presented in conventional form in the following table.

| System/Prescription Data GENERAL LENS DATA: | |
|---|---|
| Surfaces | 24 |
| Stop | 1 |
| System Aperture | Entrance Pupil Diameter = 4.5 |
| Glass Catalogs | SCHOTT |
| Effective Focal Length | −6.875823 (in air at system temperature and pressure) |
| Back Focal Length | 18.14601 |
| Total Track | 108.6794 |
| Image Space F/# | 1.527961 |
| Working F/# | 1.606138 |
| Stop Radius | 2.25 |
| Paraxial Image Height | 0.8747152 |
| Entrance Pupil Diameter | 4.5 |
| Entrance Pupil Position | 0 |
| Exit Pupil Diameter | 2.254377 |
| Exit Pupil Position | −3.439 |
| Field Type | Angle in degrees |
| Maximum Field | 7.25 |
| Primary Wave | 0.55 |
| Lens Units | Millimeters |
| Angular Magnification | −1.996117 |

| SURFACE DATA SUMMARY: | | | | | | |
|---|---|---|---|---|---|---|
| Surf | Type Conic | Comment | Radius | Thickness | Glass | Diameter |
| OBJ | STANDARD | | Infinity | Infinity | 0 | 0 |
| STO | STANDARD | | Infinity | 11 | | 4.5 | 0 |
| 2 | STANDARD | | Infinity | 1 | BK7 | 11 | 0 |
| 3 | STANDARD | | Infinity | 5 | | 11 | 0 |
| 4 | STANDARD | | 13.47504 | 2.5 | SK2 | 10 |
| 5 | STANDARD | | Infinity | 0 | | 10 | 0 |
| 6 | STANDARD | | Infinity | 2 | | 9 | 0 |
| 7 | STANDARD | | −48.37569 | 0 | SF2 | 9 |
| 8 | STANDARD | | −48.37569 | 2 | SF2 | 10 |
| 9 | STANDARD | | 12.38088 | 0.95 | | 9 | 0 |
| 10 | STANDARD | | Infinity | 1.316323 | | 0 | 0 |
| 11 | STANDARD | | 27.50063 | 0 | | 9 | 0 |
| 12 | STANDARD | | 27.50063 | 2.5 | SK2 | 10 |
| 13 | STANDARD | | −27.50063 | 28.83199 | | 10 |
| 14 | STANDARD | | Infinity | 10.44068 | | | 9.159154 |
| 15 | STANDARD | | Infinity | 2 | F2 | 16 | 0 |
| 16 | STANDARD | | 16.00501 | 9 | BK7 | 16 |
| 17 | STANDARD | | −16.00501 | 1 | | 16 | 0 |
| 18 | STANDARD | | Infinity | 0 | | 16 | 0 |
| 19 | STANDARD | | 16.00501 | 9 | BK7 | 16 |

-continued

SURFACE DATA SUMMARY:

| Surf Type Conic | Comment | Radius | Thickness | Glass | Diameter |
|---|---|---|---|---|---|
| 20 STANDARD | | −16.00501 | 2 | F2 | 16 |
| 21 STANDARD | | Infinity | 0 | 16 | 0 |
| 22 STANDARD | | Infinity | 14.70141 | 4.5 | 0 |
| 23 PARAXIAL | | — | 3.439 | 2.755904 | — |
| IMA STANDARD | | Infinity | — | 1.8225 | 0 |

Other designs are possible for providing an angular magnification of 1.5–3× as long as the ratio of the objective focal length and eyepiece focal length is 1.5–3. For example, in this system, the eyepiece has a focal length of 18 mm, and the objective has a focal length of 36 mm. It is also possible, for example, to design a system with an eyepiece focal length of 24 mm and an objective focal length of 48 mm. The particular focal lengths were chosen as a tradeoff of system length and lens complexity. The shorter the focal lengths are, the more complex and expensive the lenses become. Again, FIGS. 3a through 3d show the mechanical design for the optical system.

There is an additional aspect of the design of the ocular that needs to be considered, and that is exit pupil position. It is important in the ocular design to match the position of the observer's eye with the position of the exit pupil of the entire optical system, including the endoscope. Most endoscopes have their exit pupil located near the proximal end of the endoscope eyepiece. Therefore, the image of the proximal end of the endoscope eyepiece as seen through the endoscope test system ocular must be accessible to the observer's eye. The position of the system exit pupil is adjusted by moving the distance from the endoscope eyepiece to the most distal lens of the eyepiece and is also adjusted by the ratio of the focal lengths and the particulars of the lens design. As shown in the optical design specification above, the distance from the most proximal lens of the eyepiece to the exit pupil is 14.7 mm. In addition, it will be recognized that the exit pupil of the ocular in the above example is one-half the diameter of the exit pupil of the tested endoscope so the brightness of display images have to be adjusted accordingly.

Figure 4:
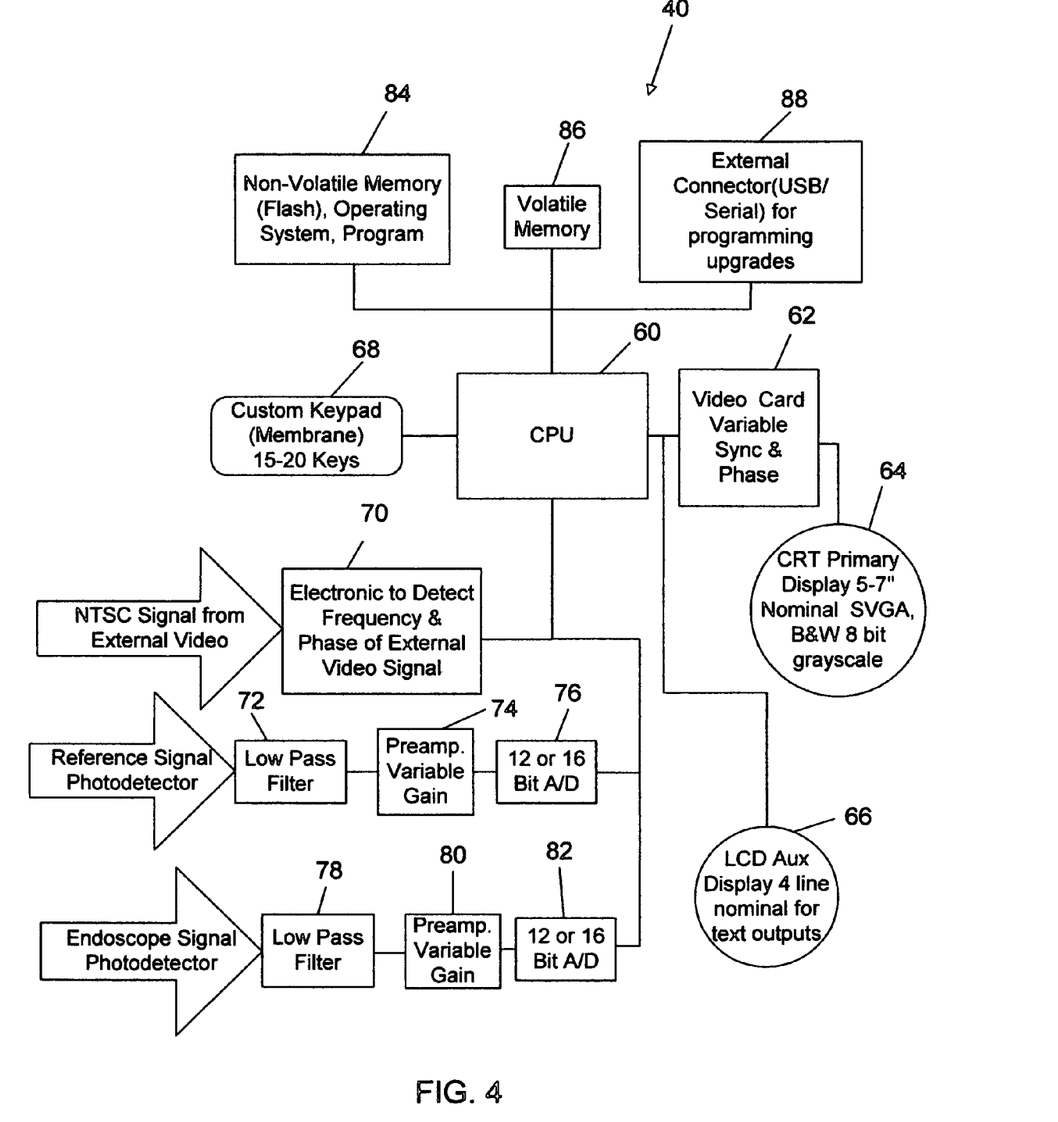
FIG. 4 is a high level schematic of the electronic display control and data processing features of the invention.

As mentioned earlier, an endoscope 28 is positioned in front of a CRT or video monitor controlled by an imbedded processor that forms part of electronic display control and data processing subsystem 40. FIG. 4 shows the electronic flowchart for the embedded system display control and data processing subsystem 40. As seen there, subsystem 40 comprises a CPU 60, a video card 62 possessing a variable sync and phase, a CRT 64 and a custom keypad 68. An auxiliary LCD display 66 may be provided, for example, for 4 line text outputs. External NTSC external video signals are sent through connector 146 to electronics component 70 to detect their frequency and phase before being passed to the CPU 60.

A reference signal photodetector is passed to CPU 70 via a low-pass filter 72, a preamp 74 and an A/D converter 76 to provide a basis for assessing transmission and vignetting of an endoscope. Likewise, an endoscope signal photodetector is passed to the CPU 60 via low-pass filter 78, preamp 80 and A/D converter 82. Either photodetector may be provided with collection optics as needed for gathering the relevant target light for performing vignetting and/or transmission tests to be more fully described hereinafter.

System memory is provided in two forms as non-volatile memory 84 and volatile memory 86 for purposes of storing code, data, graphics, libraries, and performing updates. External connectors 88 are provided as, for example, USB and serial ports to connect with peripherals.

Figure 11:
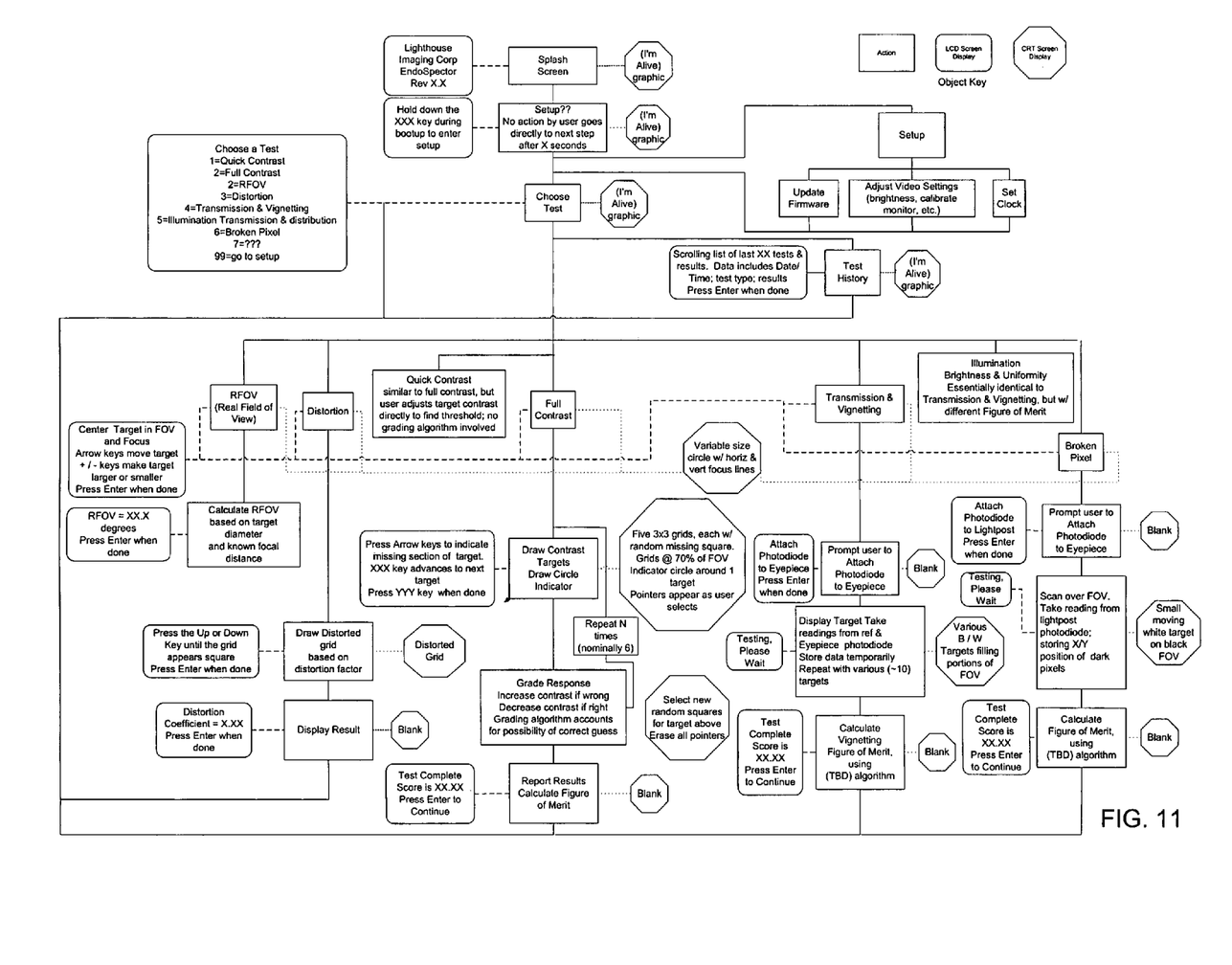
FIG. 11 is a flowchart of the flow of operations of the software during execution of the inventions various testing and calibration procedures.

Having described the mechanical, electronic and optical aspects of the invention, the methodology which is used to test endoscopes will now be described. In carrying out the various test procedures made possible by the invention, reference may be had to the software flowchart appearing in FIG. 11 along with the following description. As will appreciated, the underlying code for implementing the software may be provided using conventional software techniques and computer programming languages.

Figure 5:
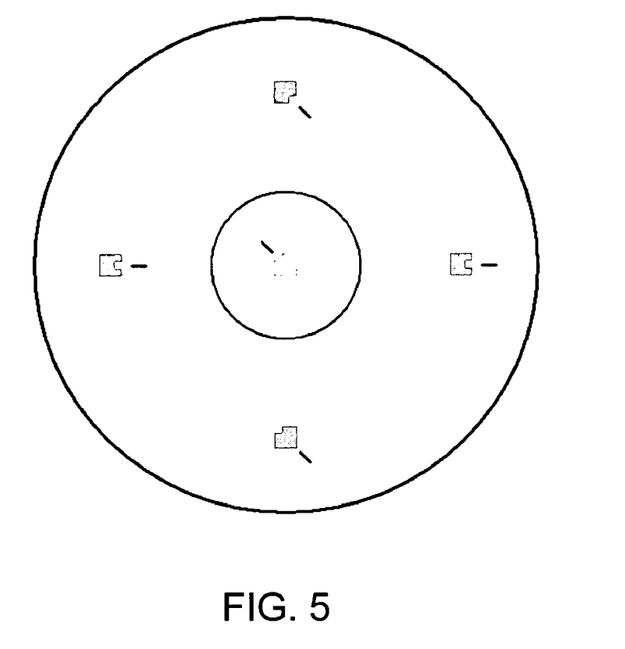
FIG. 5 is a diagrammatic view of a test target presented to the endoscope during a contrast test procedure; the test target being electronically generated as an image on a display serving as an object to the endoscope.
Figure 6:
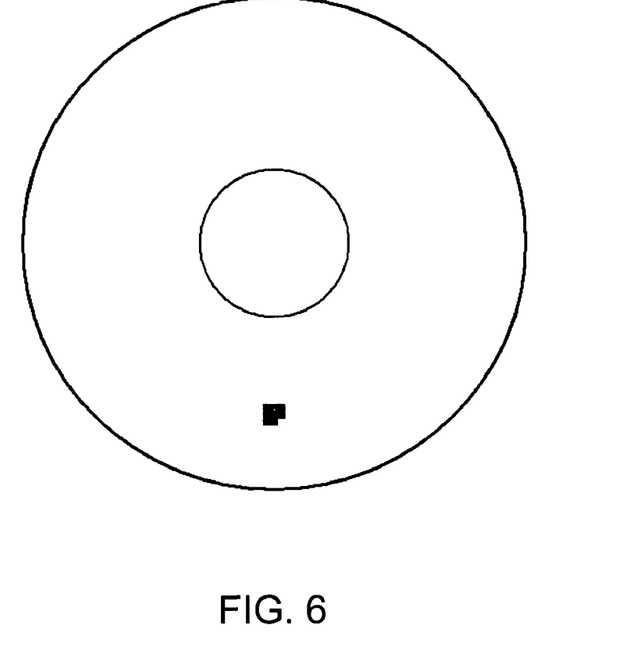
FIG. 6 is a diagrammatic view of another test target presented to the endoscope during a contrast test procedure in response to an incorrect test selection by an operator about the contents of a prior test target; the test target also being electronically generated as an image on a display serving as an object to the endoscope.
Figure 7:
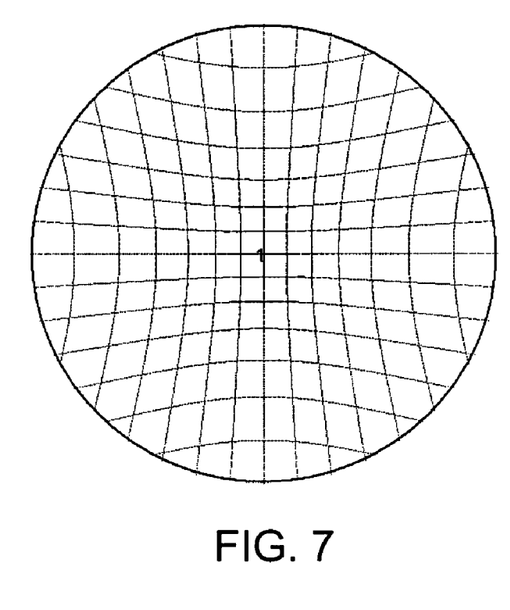
FIG. 7 is a diagrammatic view of a test target presented to the endoscope during a distortion test procedure; the test target being electronically generated as a grid with a predetermined amount of distortion.

The most important test of an endoscope is its contrast performance at various levels of target detail since this measures its visual acuity. The process for performing a contrast measurement is as follows. The user adjusts the diameter of a target by pressing keyboard keys that are provided to increase and decrease the diameter of the CRT image. Other keyboard keys move the CRT image up, down, right, and left so that the outer ring is coincident with the outer edge of the endoscope field of view. The user then focuses the ocular 24 so the target is most clearly seen. It should be noted that the field of view of the endoscope, an important specification of an endoscope, can now be easily calculated by the computer when the distance from the scope tip to the target is known. The test begins by the user noting and entering with an input device, such as the keyboard 68, which section of the center target square (e.g., a 3×3 array) has a notch cut into it (See FIG. 5). Alternatively, the square can be replaced by a ring with a section missing (e.g., C) or by an x in one corner of the cente target square. The procedure is repeated at the other field positions. In the example of FIG. 5, there are 4 field positions around the periphery of the field of view and one field position in the center of the field of view. A further input evaluates which inputs were entered correctly by the user, and which were incorrect. This is done by the system since it knows a priori the correct input and can compare the actual user selection against what it should be. If the input is correct, the next test at that field position displays a lower contrast target, and the measurement is repeated. Changes to the display can be randomly selected. If the input is incorrect, the next test at that field position displays a higher contrast target as illustrated in FIG. 6. Also, note that in FIG. 7 those targets that were identified correctly, now have a lower contrast. Alternatively, a correct input can sequentially display smaller or larger target elements. Also, the scale of the array, the contrast among its pixels, and the presence or absence of pixels can be selectively designed or randomly varied. The measurement repeats a given number of times, usually between 6 and 12 to iteratively determine the limit of resolution of the endoscope. The system automatically keeps track of scoring using various statistical techniques that are employed to make the approach to the limiting resolution more efficient so the test can be concluded-more quickly. In this process, the statistics are preferably adjusted to account for the probability of the user making a chance correct guess. In the example in FIG. 5, the user has entered correct positions for the missing notch in all field positions except the bottom target. FIG. 6 shows the next target display with a lower contrast target in all field positions except the bottom, which displays a higher contrast target. A quick test may be conducted with alternative software so that the user controls the decrease in contrast and self-assesses whether the target can be resolved.

Figure 8:
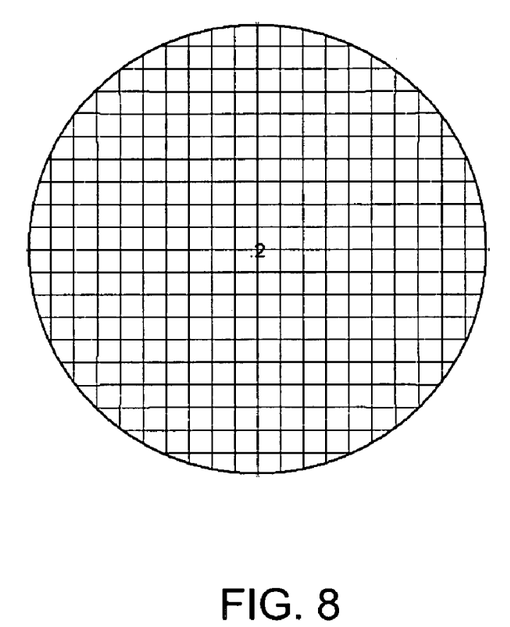
FIG. 8 is a diagrammatic view of a test target presented to the endoscope during a distortion test procedure; the test target having been electronically altered by the test system operator to cancel out the known distortion presented in the distorted grid of FIG. 7.

Distortion is measured in a manner similar to that used to measure contrast, but different images are displayed and processing differs. Here, the endoscope is positioned in front of the video monitor, again controlled by the imbedded processor. The user adjusts the diameter of the target so that the outer ring is coincident with the outer edge of the endoscope field of view. The user then focuses the ocular 24 so the target is most clearly seen. Here, the target is a grid of squares that has been generated on the display with the grid having a known, given amount of optical distortion (See FIG. 7), which is controllable by the user through an input device such as the keyboard. In FIG. 8, a schematic representation of the image seen through the invention shows a square grid, which indicates that the test endoscope has a distortion equal to the negative of the distortion introduced on the display. Thus, one can easily deduce the amount of endoscope distortion as being the negative of the displayed distortion when the user sees minimum distortion through the invention.

Figure 9:
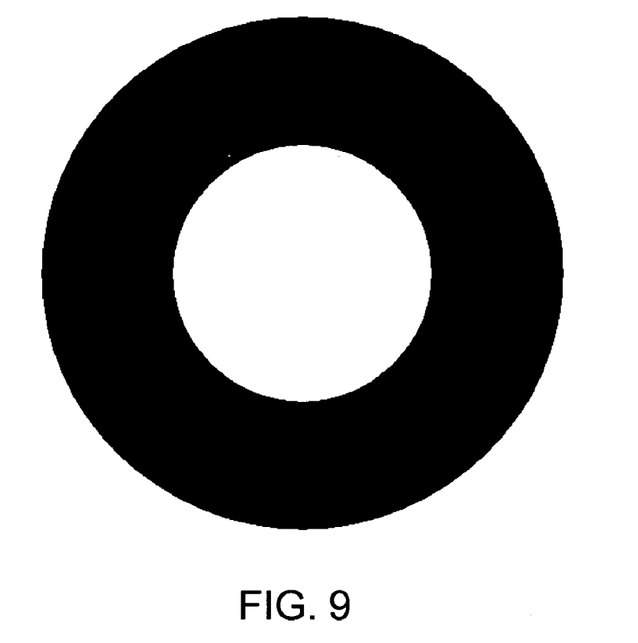
FIG. 9 is a diagrammatic view of a test target presented to the endoscope during a vignetting test procedure; the test target having been electronically generated by the test system to transmit light to the endoscope over a predetermined solid angle near the center of its field of view.
Figure 10:
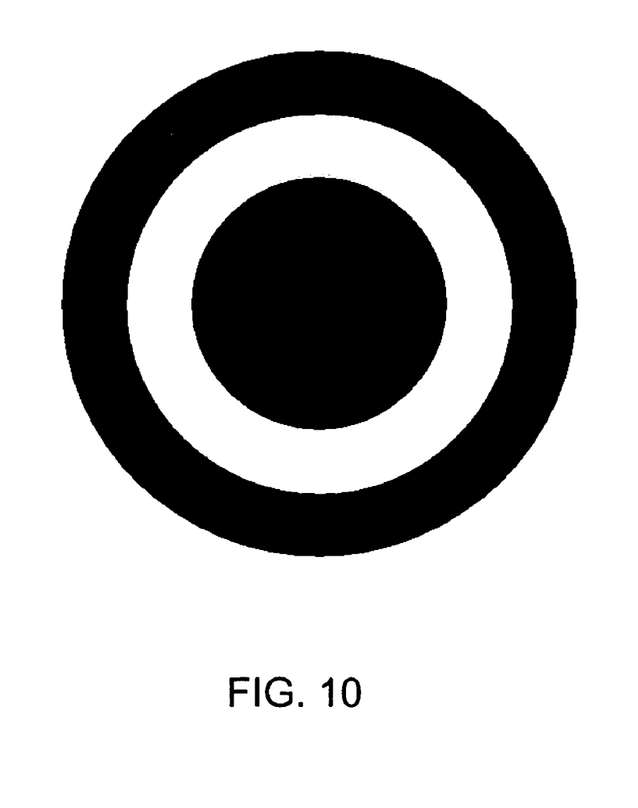
FIG. 10 is a diagrammatic view of a another test target presented to the endoscope during a vignetting test procedure; the test target having been electronically generated by the test system transmit light to the endoscope over a predetermined range of field angles located off the axis of the endoscope's field of view.

Another important measurement that is performed with the invention is vignetting. Vignetting measures the difference in the brightness of an endoscope between the center of the field of view and the periphery of the field of view. Similar to the contrast measurement above, the endoscope is positioned in front of a video monitor controlled by the imbedded processor. The user adjusts the diameter of the target so that the outer ring is coincident with the outer edge-of the endoscope field of view. The user then focuses the invention ocular 24 so the target is most clearly seen. The user then places a detector, preferably a large area silicon photodiode (See FIG. 4), near the invention eyepiece such that the active area of the detector measures essentially all of the light passing through the optical system. The user begins the measurement with an input device such as a keyboard. The video display first displays a target similar to FIG. 9 so that the detector receives and measures significant light only from the center of the field of view. The video display then displays a target similar to FIG. 10 so that the detector receives and measures significant light only from the periphery of the field of view. The signals are then ratioed in the conventional way and combined with reference photodetector levels (Again See FIG. 4) to calculate vignetting. Transmission may also be calculated by performing the vignetting test using only a uniformly illuminated target.

Another similar test that can be employed is endoscope fiberoptic illumination and illumination distribution. Fiberoptic illumination distribution measures the difference in the fiberoptic illumination of an endoscope between the center of the field of view and the periphery of the field of view. Similar to the contrast measurement above, the endoscope is positioned in front of a video monitor controlled by the imbedded processor. The user adjusts the diameter of the target so that the outer ring is coincident with the outer edge of the endoscope field of view. The user then focuses the invention ocular 24 so the target is most clearly seen. The user then places a detector, preferably a large area silicon photodiode (See FIG. 4), near the endoscope illumination input sidearm such that the active area of the detector measures essentially all of the light passing through the fiberoptic system. The user begins the measurement with an input device such as a keyboard. The video display first displays a target similar to FIG. 9 so that the detector receives and measures significant light only from the center of the field of view. The video display then displays a target similar to FIG. 10 so that the detector receives and measures significant light only from the periphery of the field of view. The signals are then ratioed in the conventional way and combined with reference photodetector levels (Again See FIG. 4) to calculate fiberoptic illumination distribution. Fiberoptic illumination may also be calculated by performing the fiberoptic illumination test using only a uniformly illuminated target.

Another test is endoscope light cable transmission. This test is similar to the fiberoptic illumination test but instead of testing the internal endoscope fiberoptic illumination, the endoscope light cable transmission test measures the light cable that is used to transmit light from the light source to the endoscope illumination input sidearm.

Another test that can be employed involves evaluating a fiber based endoscope for the presence of a broken fiber in its coherent bundle. Here, a small white pixel array (e.g., 3×3 array) is moved across an otherwise black monitor field while an eyepiece detector monitors light level. If a fiber is broken, the light level drops at the corresponding field position.

Once all, or one or more, of the individual tests have been performed, a weighting function can be employed to arrive at a collective figure of merit representing the fitness of an endoscope for clinical use based on the constellation of tests performed at various field positions. For example, the measurement at the center of the field of view may be weighted more heavily than measurements at the periphery of the field of view. Also, an endoscope with a poor performance at any one field position may be penalized more strongly. For example, a weighting function mya be $½*center+¼*average\ edge+¼*minimum\ edge$. The individual weight assigned to the outcome of any one test is determined by experience and expected performance, and previous history on any particular endoscope.

Having described specific embodiments of the invention, variants of those embodiments will occur to those skilled in the art base on its teachings. For example, it is possible to configure the endoscope tester so that the targets are simple slides that may be front or back lit. Using the ocular with magnification would still reduce the effects of eye resolution on the measurement results. While not as convenient as electronic targets, benefit would still exist by using this approach with the magnifying ocular. In addition, endoscopes of the type that use solid state image detectors located, for example, at their distal ends can also be tested by displaying video test images to serve as the object for the distal end detector, typically a CCD array. Here, the distal end detector generates a video signal that is passed to a video monitor, which is then observed by a user, and scores are tabulated in the previously described manner. In such systems, it is necessary to assure that all displays are properly synchronized with one another, otherwise have compatible pixel geometries, and any optical image degradations introduced by the test components themselves be compensated. If, for example, a problem exists because of incorrect video synchronization between the endoscope and video test signals, the familiar horizontal black bar pattern is produced that may roll repeatedly up or down across the width of the display monitor. In typical systems, when this problem exists, the solution is to connect the synchronization signals of the camera and the monitor so only one synchronization signal operates both. Unfortunately, because a variety of different, endoscopes from different manufacturers may be measured with the inventive device and because a synchronization signal from the endoscope may not be available, this procedure is not possible. However, in most endoscopes, there exists a connection for users to connect a VCR or other NTSC device to the endoscope. It is possible, therefore, to extract a synchronization signal from this connection which signal can be used to display the video test signal and also to generate software using user-controllable analog to digital inputs on the test computer CPU to measure the frequency and phase of the endoscope video-signal and then set the video signal of the test specific images to a matching configuration, thereby eliminating the rolling black bar.

Other variants will be also be apparent and are intended to be within the scope of the invention.

What is claimed is:

1. An endoscope measurement apparatus, said apparatus comprising:
   a video device for displaying images;
   means for mounting an endoscope to be tested so that it can view images formed on said display and form an image thereof located at the proximal end of the endoscope;
   an ocular for observing an enlarged image of said image formed at the proximal end of the endoscope being tested to reduce the effects of eye resolution on measurement results; and
   electronic means for generating test specific images on said video device in response to user initiation and selection, prompting the operator to score his visual responses to the various displayed images, automatically changing the characteristics of the displayed images in response to user scores, recording the operator's scores and corresponding images, and determining a figure of merit for the fitness of an endoscope for clinical use.

2. The apparatus of claim 1 wherein the magnification of said ocular is at least 1.5X.

3. The apparatus of claim 1 wherein said electronic means is configured and arranged so that an endoscope can be tested for one or more figures of merit selected from the group consisting of contrast, distortion, vignetting, transmission, field of view, fiberoptic illumination transmission, and light cable transmission.

4. The apparatus of claim 1 wherein said electronic means is configured and arranged so that an endoscope can be tested for its limiting resolution.

5. The apparatus of claim 1 wherein said electronic means is configured and arranged so that an endoscope can be tested for its contrast by selectively changing the contrast of at least a portion of a displayed image.

6. The apparatus of claim 1 wherein said electronic means is configured and arranged to sequentially generate a center-transmitting target and of an edge-transmitting target so that an endoscope can be tested for vignetting, fiberoptic illumination distribution, and light cable transmission.

7. The apparatus of claim 1 wherein said electronic means is configured and arranged to sequentially generate a plurality of different and known distortion targets and assessing which target counteracts the intrinsic distortion of the endoscope.

8. The apparatus of claim 1 wherein said electronic means is configured and arranged to determine the fitness of an endoscope for clinical purposes based on a weighted average of one or more of the tests performed at different field positions.

9. The apparatus of claim 1 wherein said electronic means is configured and arranged to adjust the calculation of the figure of merit by taking into account the probability that an observer will make a correct choice by chance.

10. The apparatus of claim 1 wherein at least one of said test specific images is a rotatable square pattern with a distinct pattern in one side.

11. The apparatus of claim 1 wherein at least one of said test specific images is formed of an array of pixels where one or more of said pixels may be randomly removed or altered.

12. The apparatus of claim 1 wherein at least one of said test specific images is a distorted grid.

13. An endoscope measurement apparatus, said apparatus comprising:
    a device for displaying images;
    means for mounting an endoscope to be tested so that it can view images formed on said display and form an image thereof located at the proximal end of the endoscope; and
    a telescopic ocular for observing an enlarged image of said image formed at the proximal end of the endoscope being tested to reduce the effects of eye resolution on measurement results.

14. The apparatus of claim 13 wherein the magnification of said telescopic ocular is at least 1.5X.

15. The apparatus of claim 13 further including a video display and electronic means for generating test specific images on said video device in response to user initiation and selection, prompting the operator to score his visual responses to the various displayed images, automatically changing the characteristics of the displayed images in response to user scores, recording the operator's scores and corresponding images, and determining a figure of merit for the fitness of an endoscope for clinical use.

16. An endoscope measurement apparatus, said apparatus comprising:
    a video device for displaying test images;
    means for mounting an endoscope to be tested so that it can view test images formed on said video device and form an image thereof;
    means for viewing said image formed by the endoscope being tested; and
    electronic means for generating test specific images on said video device in response to user initiation and selection, prompting the operator to score his visual responses to the various displayed test images, automatically changing the characteristics of the displayed test images in response to user scores, recording the operator's scores and corresponding test images, and determining a figure of merit for the fitness of an endoscope for clinical use.

17. The endoscope measurement apparatus of claim 16 wherein said endoscope comprises a video detector for generating a video signal of the test image displayed on said video device and wherein said means for viewing an image formed by an endoscope comprises a video monitor.

18. The apparatus of claim 16 wherein said electronic means is configured and arranged so that an endoscope can be tested for its contrast by selectively changing the contrast of at least a portion of a test image.

19. The apparatus of claim 17 further including means for establishing video synchronization between the endoscope and the test specific images.

20. The apparatus of claim 19 wherein said means for establishing video synchronization comprises computer software for adjusting said electronic means for generating said test specific images, such software being adapted to use user-controllable analog to digital inputs on the test computer CPU to measure the frequency and phase of the endoscope video signal and then setting the video signal of the test specific images to a matching configuration.

21. An endoscope measurement apparatus, said apparatus comprising:

a device for displaying images;

means for mounting an endoscope to be tested so that it can view images formed on said display and form an image thereof located at the proximal end of the endoscope;

a telescopic ocular for observing an enlarged image of said image formed at the proximal end of the endoscope being tested to reduce the effects of eye resolution on measurement results, wherein the magnification of said telescopic ocular is at least 1.5X;

a video display and electronic means for generating test specific images on said video device in response to user initiation and selection, prompting the operator to score his visual responses to the various displayed images, automatically changing the characteristics of the displayed images in response to user scores, recording the operator's scores and corresponding images, and determining a figure of merit for the fitness of an endoscope for clinical use.

* * * * *